United States Patent
Shi et al.

(10) Patent No.: US 9,682,107 B2
(45) Date of Patent: Jun. 20, 2017

(54) POSTNATAL STEM CELLS AND USES THEREOF

(71) Applicant: THE UNITED STATES OF AMERICA, as represented by the Secretary, Department of Health and Human Services, Washington, DC (US)

(72) Inventors: Songtao Shi, Los Angeles, CA (US); Pamela Gehron Robey, Bethesda, MD (US); Stan Gronthos, South Australia (AU); Masako Miura, Kyoto (JP)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 14/869,565

(22) Filed: Sep. 29, 2015

(65) Prior Publication Data

US 2016/0008404 A1    Jan. 14, 2016

Related U.S. Application Data

(63) Continuation of application No. 10/553,633, filed as application No. PCT/US03/12276 on Apr. 19, 2003, now Pat. No. 9,175,264.

(51) Int. Cl.

| | |
|---|---|
| *C12N 5/10* | (2006.01) |
| *A61K 35/30* | (2015.01) |
| *C12N 5/071* | (2010.01) |
| *C12N 5/079* | (2010.01) |
| *C12N 5/0775* | (2010.01) |
| *A61K 47/02* | (2006.01) |
| *C12N 5/077* | (2010.01) |
| *A61K 35/12* | (2015.01) |

(52) U.S. Cl.
CPC .............. *A61K 35/30* (2013.01); *A61K 47/02* (2013.01); *C12N 5/0602* (2013.01); *C12N 5/0618* (2013.01); *C12N 5/0654* (2013.01); *C12N 5/0664* (2013.01); *A61K 35/12* (2013.01); *C12N 2501/11* (2013.01); *C12N 2501/115* (2013.01); *C12N 2506/1361* (2013.01); *C12N 2533/54* (2013.01)

(58) Field of Classification Search
CPC ........................... A61K 35/30; A61K 435/367
See application file for complete search history.

(56) References Cited

FOREIGN PATENT DOCUMENTS

| | | |
|---|---|---|
| CA | 2474783 | 8/2003 |
| WO | WO 02/07679 A2 | 1/2002 |
| WO | WO 2004/094588 A2 | 11/2004 |

OTHER PUBLICATIONS

Arthur, 2008, Stem Cells, 26:1787-1795.*
Sakai, 2012, Journal of Clinical Investigation, 122:80-90.*
Huang, 2009, J Dent Res, 88:792-806.*
Gepstein, L. "Derivation and Potential Applications of Human Embryonic Stem Cells," *Circulation Research* 91:866-876 (2002).
Gronthos et al., "Postnatal Human Dental Pulp Stem Cells (DPSCs) in Vitro and in Vivo," *Proc. National Academy of Science* 97(25):13625-13630 (Dec. 5, 2000).
Gronthos et al., "Stem Cell Properties of Human Dental Pulp Stem Cells." *Journal of Dental Research* 81:531-535 (Aug. 2002).
International Search Report from parent PCT Application No. PCT/US2003/012276, 3 pages (mailed Nov. 1, 2004).
Krebsbach et al., "Dental and Skeletal Stem Cells: Potential Cellular Therapeutics for Craniofacial Regeneration," *Journal of Dental Education* 66:766-773 (Jun. 2002).
Nakashima et al, "Induction of Dental Pulp Stem Cell Differentiation Into Odontoblasts by Electroporation-Mediated Gene Delivery of Growth/Differentiation Factor 11 (Gdf11)" *Gene Therapy* 9:814-818 (Jun. 2002).
Oshiro et al., "Immunolocalization of Vacuolar-Type H+-ATPase, Cathepsin K, Matrix Metalloproteinase-9, and Receptor Activator of NFkB Ligand in Odontoclasts During Physiological Root Resorption of Human Deciduous Teeth," *The Anatomical Record* 264:305-311 (2001).
Papaccio et al., "Long-term cryopreservation of dental pulp stem cells (SBP-DPSCs) and their differentiated osteoblasts: a cell source for tissue repair," *Journal of Cellular* Physiology 208:319-325 (Aug. 2006).
Sahara et al., "A Histological Study of the Exfoliation of Human Deciduous Teeth," *Journal of Dental Research* 72(3):634-640 (1993).
Shi et al., "Comparison of Human Dental Pulp and Bone Marrow Stromal Stem Cells by cDNA Microarray Analysis," *Bone* 29:532-539 (Dec. 2001).
Shi et al., "Perivascular Niche of Postnatal Stem Cells in Human Bone Marrow and Dental Pulp," *Journal of Bone and Mineral Research* 18:696-704 (2003).
Tsukamoto et al: "Mineralized Nodule Formation by Cultures of Human Dental Pulp-Derived Fibroblasts," *Archives of Oral Biology* 37:1045-1055 (1992).

* cited by examiner

Primary Examiner — Valarie Bertoglio

(74) Attorney, Agent, or Firm — Klarquist Sparkman, LLP

(57) ABSTRACT

The invention generally relates to postnatal dental stem cells and methods for their use. More specifically, the invention relates in one aspect to postnatal dental pulp stem cells, use of the cells to generate dentin, and differentiation of the cells. In another aspect, the invention relates to human postnatal deciduous dental pulp multipotent stem cells, use of the cells to generate dentin, and differentiation of the cells.

18 Claims, 11 Drawing Sheets

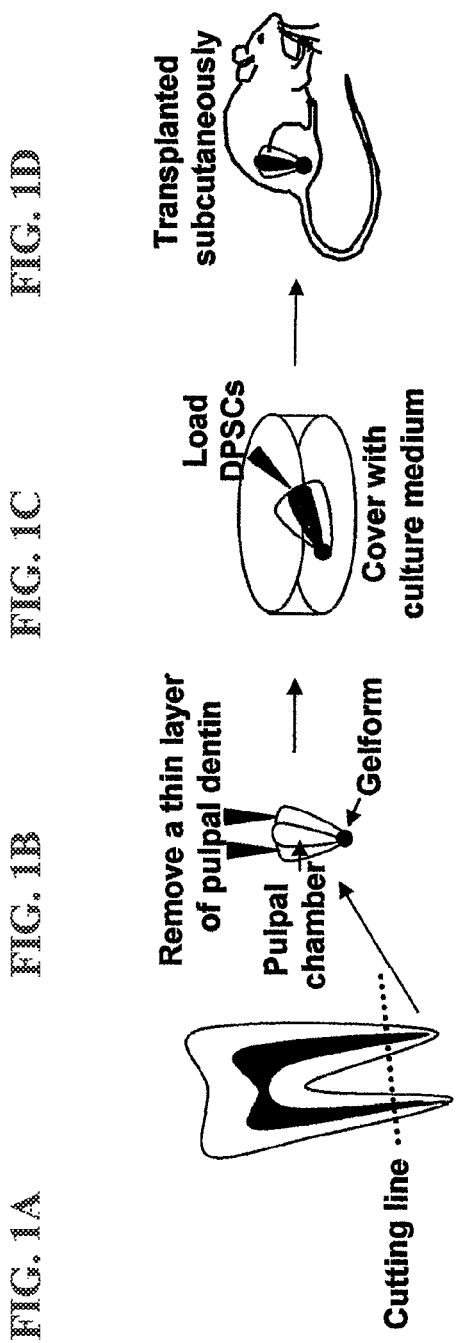

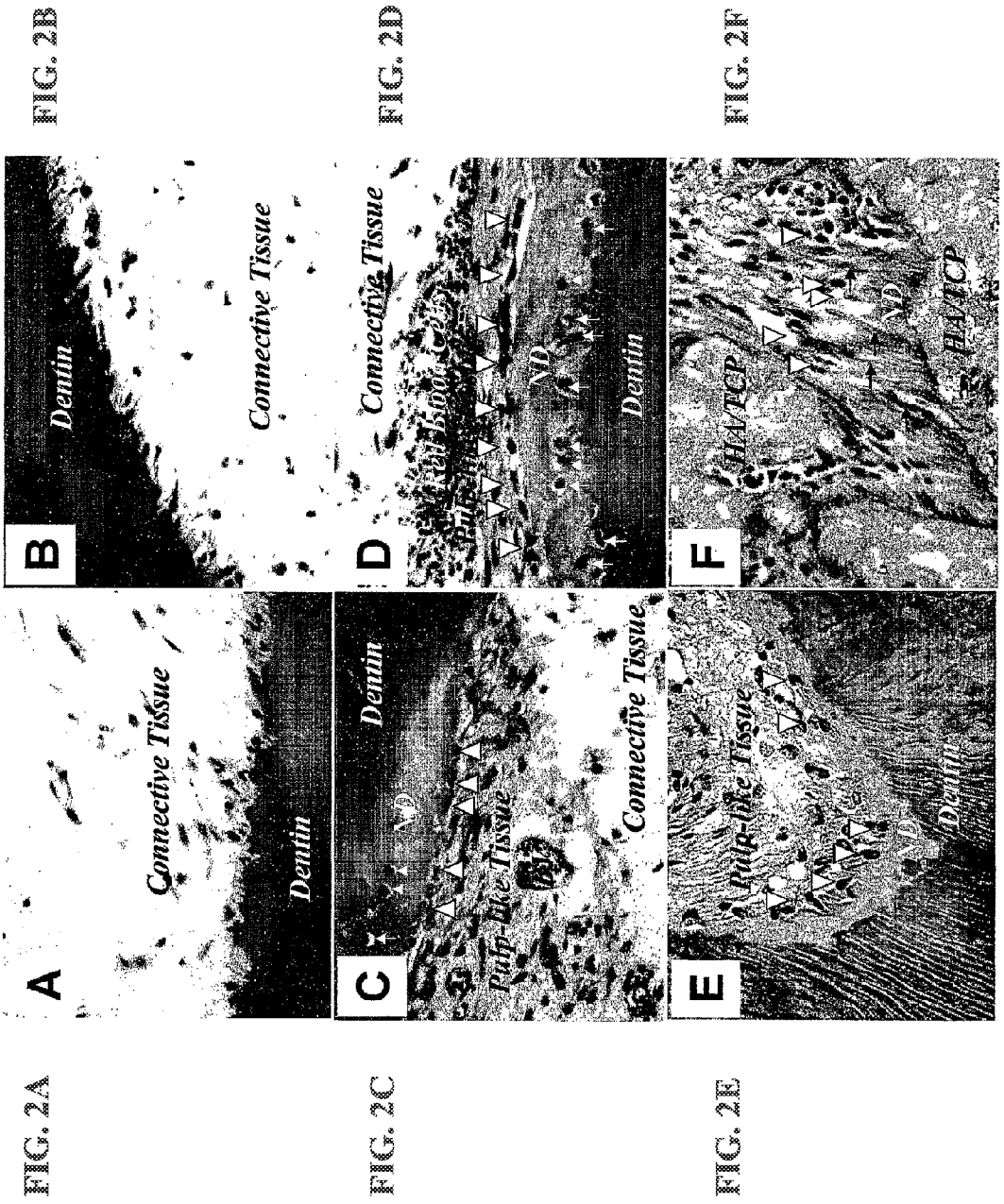

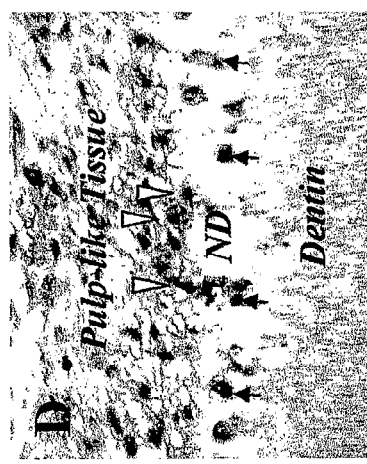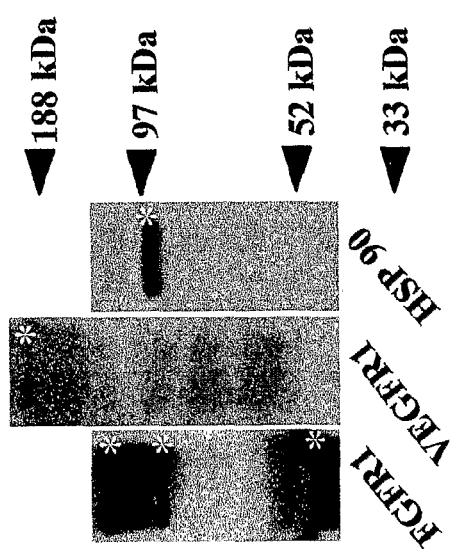

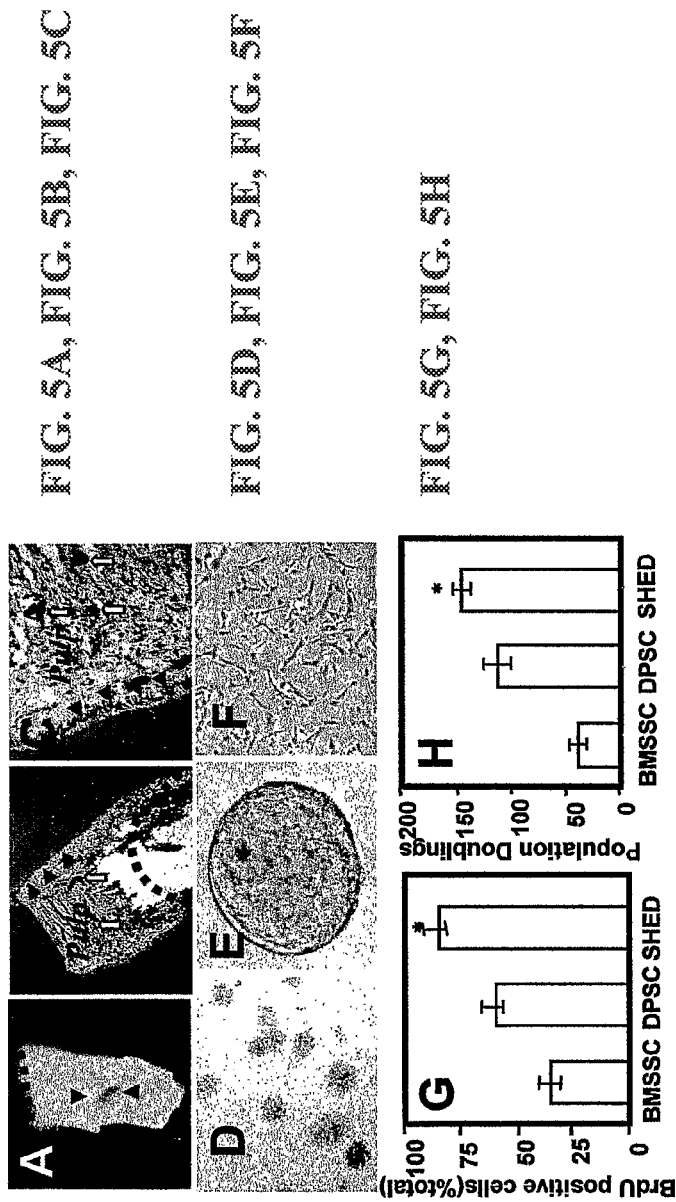

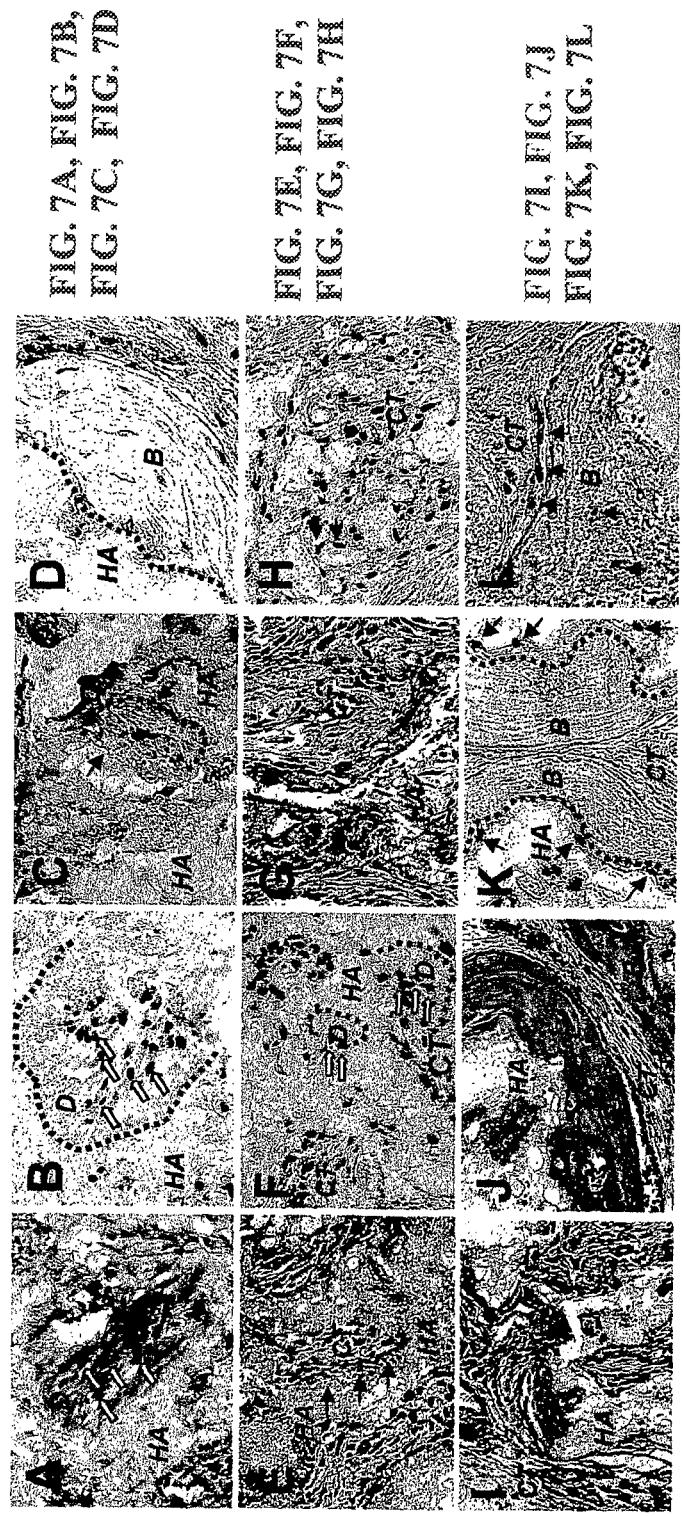

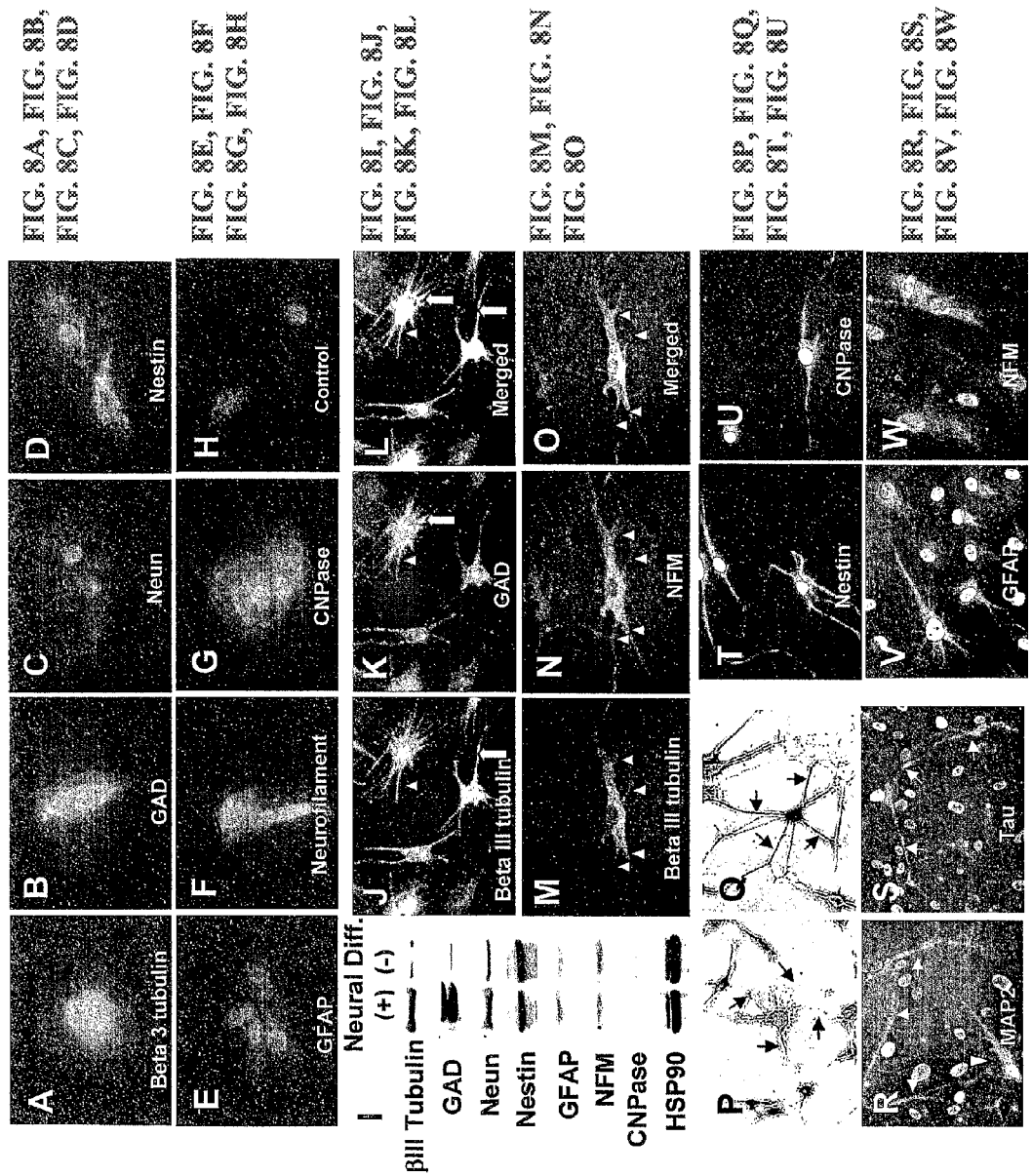

POSTNATAL STEM CELLS AND USES THEREOF

CROSS REFERENCE TO RELATED APPLICATIONS

This is a continuation of U.S. patent application Ser. No. 10/553,633, filed Nov. 7, 2006, now U.S. Pat. No. 9,175,264; which is the U.S. national stage of PCT Application No. PCT/US2003/012276, filed Apr. 19, 2003, which was published in English under PCT Article 21(2).

FIELD OF THE INVENTION

The invention generally relates to postnatal dental stem cells and methods for their use. More specifically, the invention relates in one aspect to postnatal dental pulp stem cells, use of the cells to generate dentin, and differentiation of the cells. In another aspect, the invention relates to human postnatal deciduous dental pulp multipotent stem cells, use of the cells to generate dentin, and differentiation of the cells.

BACKGROUND OF THE INVENTION

Post-natal stem cells (meaning those present after birth) are unspecialized cells that can renew themselves extensively and develop into more mature cells having specialized functions. Stem cells may be induced under certain physiologic or experimental conditions to become cells with special functions, such as the beating cells of the heart muscle, or the insulin-producing cells of the pancreas. The process by which a stem cell becomes a cell with special functions is known as differentiation. Differentiation can be induced through use of multiple signals that can include chemicals secreted by other cells, physical contact with neighboring cells, and certain molecules in the microenvironment. Thus, stem cells can be treated with specific signals to become specific types of cells having useful functions. These newly differentiated cells can then be used to generate replacements for cells that are lost through normal wear and tear, injury, or disease. For example, stem cells show promise for treating diseases such as Parkinson's disease, diabetes, and heart disease. Stem cells have multiple applications in medicine and dentistry. Accordingly, new sources of stem cells, and methods for their use are needed.

SUMMARY OF THE INVENTION

Methods and materials are provided by the current invention that address the aforementioned needs. The invention provides an isolated human postnatal deciduous dental pulp multipotent stem cell, a method to implant a bone-inducing cell within an organism, a method to implant a neural cell within an organism, a method to implant an adipocyte within an organism, and a method to generate dentin.

The invention provides an isolated human postnatal deciduous dental pulp multipotent stem cell. A human postnatal deciduous dental pulp multipotent stem cell can differentiate into a neural cell, an adipocyte, or an odontoblast. A human postnatal deciduous dental pulp multipotent stem cell can be obtained from a non-exfoliated deciduous tooth. Preferably, a human postnatal deciduous dental pulp multipotent stem cell is obtained from an exfoliated deciduous tooth (SHED). A human postnatal deciduous dental pulp multipotent stem cell can be stored for later use. A human postnatal deciduous dental pulp multipotent stem cell can be grown in tissue culture medium. Preferably, the tissue culture medium includes serum. More preferably, the tissue culture medium does not include serum. The tissue culture medium can include one or more growth factor. Preferably, the growth factor is basic fibroblast growth factor, epidermal growth factor, or both. The tissue culture medium can include a neuronal supplement. Preferably, the neuronal supplement is B27 supplement.

The invention provides a method to generate bone within an organism. Generally, the method involves implanting a human postnatal deciduous dental pulp multipotent stem cell into an organism. Preferably the organism is a mammal. More preferably the organism is a human. The human postnatal deciduous dental pulp multipotent stem cell may be obtained from one human and implanted into a different human. Preferably, the human postnatal deciduous dental pulp multipotent stem cell is obtained from, and implanted into the same human. The human postnatal deciduous dental pulp multipotent stem cell may be expanded ex vivo prior to being implanted into the organism. Preferably the human postnatal deciduous dental pulp multipotent stem cell is induced prior to being implanted into the organism. Preferably, the human postnatal deciduous dental pulp multipotent stem cell is induced with BMP-4 or mineralizing induction. A human postnatal deciduous dental pulp multipotent stem cell that is not in combination with a carrier can be implanted into an organism. A human postnatal deciduous dental pulp multipotent stem cell that is in combination with a carrier can be implanted into an organism. Preferably, the carrier contains hydroxyapatite. More preferably, the carrier contains tricalcium phosphate. Most preferably, the carrier contains hydroxyapatite and tricalcium phosphate. The human postnatal deciduous dental pulp multipotent stem cell can induce a recipient cell to differentiate into bone-forming cells. The method of the invention can be used to promote bone formation at a site of trauma within an organism. The trauma may be produced by a physical injury. Preferably the physical injury is an accidental physical injury. More preferably, the physical injury results from a medical or dental procedure. Most preferably, the physical injury results from surgery. The trauma may be due to degenerative disease. Preferably the degenerative disease is osteoporosis.

The invention provides a method to produce neural tissue within an organism. Generally, the method involves implanting a dental stem cell into an organism. Preferably, the dental stem cell is a dental pulp stem cell. More preferably, the dental stem cell is a human postnatal deciduous dental pulp multipotent stem cell. Preferably the organism is a mammal. More preferably the organism is a human. The dental stem cell can be implanted into tissue present within the organism. Preferably the tissue is neural tissue. The dental stem cell may be expanded ex vivo prior to being implanted into the organism. Preferably the dental stem cell is neuronal induced prior to being implanted into the organism. A dental stem cell that is not in combination with a carrier can be implanted into an organism. A dental stem cell that is in combination with a carrier can be implanted into an organism.

The invention provides a method to produce adipose tissue within an organism. Generally, the method involves implanting a dental stem cell into an organism. Preferably, the dental stem cell is a dental pulp stem cell. More preferably, the dental stem cell is a human postnatal deciduous dental pulp multipotent stem cell. Preferably the organism is a mammal. More preferably the organism is a human. The dental stem cell may be expanded ex vivo prior to being implanted into the organism. Preferably the dental stem cell is adipogenesis induced prior to being implanted into the organism. A dental stem cell that is not in combination with a carrier can be implanted into an organism. A dental stem cell that is in combination with a carrier can be implanted into an organism.

The invention provides a method to generate dentin by implanting a dental stem cell within an organism. The method can be used to generate dentin on pre-existing dentin by contacting the pre-existing dentin with a dental stem cell and incubating the pre-existing dentin and the dental stem cell. Preferably, the dental stem cell is a dental pulp stem cell. More preferably, the dental stem cell is a human postnatal permanent tooth dental pulp stem cell. More preferably, the dental stem cell is a human postnatal deciduous dental pulp multipotent stem cell. Preferably, the pre-existing dentin is contacted with the dental stem cell in vitro. More preferably, the pre-existing dentin is contacted with the dental stem cells in vivo. The pre-existing dentin can be contained within a tooth. The dental stem cells can be obtained from the tooth of a mammal. Preferably, the dental stem cell is obtained from the tooth of a human. More preferably, the dental stem cell is obtained from a human permanent tooth. Most preferably, the dental stem cell is obtained from a human deciduous tooth. The pre-existing dentin can be from a mammal. Preferably, the pre-existing dentin is from a human. The pre-existing dentin and the dental stem cell can be obtained from different mammals. More preferably, the pre-existing dentin and the dental stem cell is obtained from the same mammal. Most preferably, the pre-existing dentin and the dental stem cell is obtained from the same human. The pre-existing dentin can be contacted with a formulation to produce treated dentin. Preferably, the pre-existing dentin is contacted with a formulation after the pre-existing dentin is contacted with a dental stem cell. More preferably, the pre-existing dentin is contacted with a formulation before the pre-existing dentin is contacted with a dental stem cell. Preferably, the formulation is a base solution. More preferably, the formulation is an acid solution. Most preferably, the formulation is an acetic acid solution. The treated dentin can be washed with a fluid. Preferably, the fluid is a biological solvent. More preferably, the fluid is water. Even more preferably, the fluid is a biological buffer. Most preferably, the fluid is phosphate buffered saline. The pre-existing dentin can be contacted with a dental stem cell that is not in combination with a carrier. The pre-existing dentin can be contacted with a dental stem cell that is in combination with a carrier. Preferably, the carrier contains hydroxyapatite. More preferably, the carrier contains tricalcium phosphate. Most preferably, the carrier contains hydroxyapatite and tricalcium phosphate. The method of the invention can be used to generate dentin in response to trauma to a tooth.

Preferably the trauma is erosion of the tooth. More preferably, the trauma results from dental treatment. Most preferably, the trauma results from a root canal procedure.

SEQUENCE LISTING

The Sequence Listing is submitted as an ASCII text file [4239-81540-12_Sequence_Listing.txt, Sep. 25, 2015, 3.27 KB, which is incorporated by reference herein.

BRIEF DESCRIPTION OF THE DRAWINGS

FIGS. 1A-1D are diagrams showing the preparation of a dentin scaffold, culturing DPSCs, and implanting a dentin/DPSC-complex into an immunocompromised mouse. (A) Root tips from extracted third molars were cut off on the indicated cutting line and the root foramen was sealed with Gelfoam. (B) Pulp tissue and a layer of pulpal dentin were removed from the root tip and then treated with 1% acetic acid for 10 minutes. (C) After PBS washing, DPSCs were loaded onto the dentin surface of the pulpal chambers and cultured at 37° C. for 12 hours in 10 cm cell culture dishes with 15 ml of culture medium covering the whole root tips. (D) DPSC/dentin complex was implanted into immunocompromised mice subcutaneously.

FIGS. 2A-2F show the dentinogenesis of human DPSCs in vivo. (A) Implanted acid-treated dentin vehicle without any cells, there was only connective tissue around dentin surface. (B) Skin fibroblasts were loaded on the acid-treated dentin and cultured for 12 hours, then fibroblast/dentin complexes were implanted into immunocompromised mice. There was connective tissue around the dentin surface without any new dentin formation eight weeks after implantation. (C-E) Newly formed dentin (ND) was associated with human dentin scaffold (Dentin) and pulp-like tissue containing odontoblasts (open triangles) blood vessel (BV) eight weeks after implantation of the DPSC/dentin complexes. The newly formed dentin may contain trapped cellular components (white arrows in C and D) or only odontoblasts responsible for a thin layer of dentin formation (ND in E). The pulp-like tissue was defined as a cell rich connective tissue containing blood vessels (BV), red blood cells, and odontoblasts (open arrows) lining on the surface of newly formed dentin, which was different from regular connective tissue containing a limited number of cells (C and D). (F) DPSCs were implanted with HA/TCP as a carrier to show odontoblasts (open arrows) were responsible for the newly formed dentin (ND) with tubule structure (black arrows) on the surfaces of HA/TCP (HA). Sections were stained with hematoxylin and eosin. Original magnification is 40×.

FIGS. 4A-4E show the expression of FGF and VEGF receptors in human DPSCs. (A and B) FGF receptor 1 (A) and VEGF receptor 1 (B) expressed in cultured human DPSCs at 25 population doublings. Light grey (red in color photo) represents positive staining and medium grey (blue in color photo) shows nuclei staining of DAPI. (C) Western blot analysis confirmed the expression of these molecules in cultured DPSCs. Asterisks represent immunopositive bands. HSP90 was used to show protein loading per sample. (D-E) DPSC/dentin implants at eight weeks post-implantation, dentinogenic cells (black arrows) trapped inside newly formed dentin (ND) were immunopostive for FGF receptor 1 antibody (D) and VEGF receptor 1 antibody (E). However, odontoblasts were only immunoreactive for FGF receptor 1 antibody (open arrows in D). Original magnification is 40× for A-B and D-E.

FIGS. 5A-5H illustrate isolation of SHED. (A) The exfoliated primary incisor contained dental pulp as shown (triangles). The dashed line shows the occlusion edge of the incisor. (B and C) Hematoxylin and eosin staining indicated dentin (D) and pulp (pulp) of exfoliated deciduous teeth. The pulp contained odontoblasts (arrows), blood vessels (open arrows), and connective tissues. The straight and curved dash lines in (B) represent the occlusion and resorbed root surfaces, respectively. (D) Single colonies were formed after SHED were plated at low density and cultured for two weeks. (E) SHED were capable of forming sphere-like clusters when cultured with the conditions described in the Methods. (F) The sphere-like clusters could be dissociated by passage through needles and subsequently grew on 0.1% gelatin coated dishes. (G) The proliferation rates of SHED, BMSSCs, and DPSCs were assessed by bromodeoxyuridine (BrdU) incorporation for 12 hours. SHED showed a significantly higher proliferation rate in comparison with BMSSCs and DPSCs (*$P<0.05$; Student t test). (H) SHED were able to proliferate to over 140 population doublings, which was significantly higher (*$P<0.05$; Student t test) than BMSSCs and DPSCs.

FIGS. 7A-7L show implanted SHED in immunocompromised mice. (A and B) Eight weeks after implantation, SHED were able to differentiate into odontoblasts (open arrows) that were responsible for the dentin-like structure (D) formation on the surfaces of hydroxyapatite tricalcium (HA) (A). The same field is shown for human-specific alu in situ hybridization indicating the human origin of odontoblasts (open arrows, B). The black dashed line represents interface between newly formed dentin (D) and HA/TCP (HA). (C) Immunohistochemical staining of anti-DSPP antibody shows a positive staining on the regenerated dentin (black arrows). (D) In contrast to DPSC implants, newly generated bone (B) by host cells in the same SHED implant shows no reactivity to the DSPP antibody. (E) Of 12 selected single-colony derived SHED strains, only three (25%) were capable of generating dentin in vivo. Newly formed dentin (arrows) was found to be adjacent to the surfaces of HA/TCP carrier (HA) and associated with connective tissue (CT). (F) Human-specific alu in situ hybridization showed that human cells (open arrows) were associated with dentin formation (D) and were residing within the connective tissue compartment (CT). (G) The remaining 75% (9 of 12) single-colony derived SHED strains were unable to generate dentin in vivo. (H) In situ hybridization demonstrated that alu-positive human cells survived in the connective tissue compartment (CT) in the implants in which there was no odontogenesis. Human cells were also found to surround the blood vessels (arrows). (I) 7 of 12 (58.4%) single-colony derived SHED lines induced a very limited amount of bone formation (B) on the surface of HA/TCP (HA). (J) 5 of 12 (41.6%) single-colony derived SHED lines were able to induce significant amount of bone formation (B) on the surfaces of HA/TCP (HA). (K) The alu in situ hybridization showed human cells (arrows) attached to the surfaces of HA/TCP (HA) at the initial site of bone formation (B). The black dash lines represent the interface between newly formed bone (B) and HA/TCP (HA). (L) In situ hybridization studies showed the murine-specific pf1 DNA probe reacting with osteoblasts and osteocytes (arrows) associated with the new bone formation (B).

FIGS. 8A-8W illustrate neural differentiation of SHED. (A-H) Immunocytochemical staining depicts SHED expressing Nestin, GFAP, Neurofilament M, CNPase, Beta III tubulin, GAD, NeuN. (I) Western blot analysis confirmed that SHED expressed neural markers as described above. After four weeks of culture in the presence of B27 supplement, bFGF (40 ng/ml), and EGF (20 ng/ml) (Neural diff.+), expression levels of beta III tubulin, GAD, and NeuN were up-regulated when compared with regular culture conditions as described in the Methods (Neural diff−). However, expression levels of Nestin, GFAP, CNPase, and Neurofilament remained the same following the treatment. (J-0) SHED may co-express neuronal markers including beta III tubulin (J and L, green in color photo)/GAD (K and L, red in color photo) and beta III tubulin (M and O; green in color photo)/NFM (N and 0, red in color photo). The morphology of SHED showed elongated cell-cytoplasmic processes that sometimes co-express neural markers (triangles) or only express individual neural marker (open arrows). (P-S) Toluidine blue (0.1%) staining depicting the altered morphology of SHED after induction with neural culture medium (P and 0, arrows) Immunopositive staining for anti MAP2 and Tau antibodies on dendrites and axon (R and S, arrows), respectively. Double staining experiments showing beta III tubulin positive cells were also detected in the same field (R, triangle, green in color photo). (T-W) SHED continued to express glial cell markers including Nestin (T, red in color photo), CNPase (U, red in color photo), GFAP (V, red in color photo), and neurofilament (W, green in color photo) by immunocytostaining.

DETAILED DESCRIPTION OF THE INVENTION

Figures 3A, 3B, 3C, 3D:
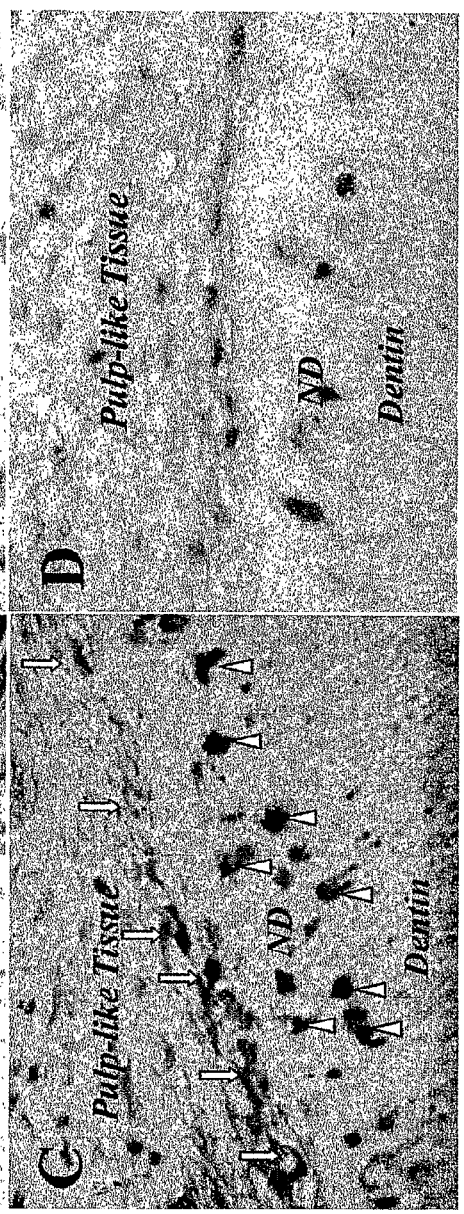
FIGS. 3A-3D show the characterization of a DPSC/dentin implant. (A) DSP immunohistochemical staining on fibroblast/dentin implant showed a positive staining on the peritubular dentin (black arrows). Connective tissue showed a negative immunostaining for DSP antibody. (B) In DPSC/dentin implants, odontoblasts (open arrows) and cells trapped inside newly formed dentin (open triangles in ND) were immunoreactive for human DSP antibody. Human dentin scaffold (Dentin) showed a DSP immunostaining on peritubular structures (black arrows). Pulp-like tissue was immunonegative for DSP antibody staining. (C) Immunohistochemical staining of human-specific anti-mitochondria antibody showed human DPSCs differentiated into odontoblasts (open arrows) lining on the surfaces of newly generated dentin (ND) and also became dentinogenic cells (open arrows) trapped inside newly formed dentin (ND). (D) Negative control of immunohistochemical staining on DPSC/dentin implant without primary antibody. Original magnification is 60×.

The invention includes human postnatal deciduous dental pulp multipotent stem cells. It was surprisingly discovered that human deciduous teeth contain progenitor cells that can give rise to diverse cell types (multipotent stem cells). This discovery was surprising because the presence of multipotent stem cells in human deciduous teeth has never been reported before. Rather, past studies were conducted with animals models having continuously erupting teeth, or were conducted with fetal material. Because human teeth do not continuously erupt, they are thought to be different from the animal models based on continuous tooth eruption.

Stem cells isolated from human exfoliated deciduous teeth have been abbreviated herein as SHED (stem cells from human exfoliated deciduous tooth). SHED are included within the group of human postnatal deciduous dental pulp multipotent stem cells. SHED have been characterized as being highly proliferative, clonogenic cells capable of differentiating into a variety of cell types. These cell types include neuronal cells, adipocytes, and odontoblasts. SHED were also found to be able to induce bone formation, generate dentin, and survive in mouse brain. SHED have also been found to express neural markers. These stem cells derived from exfoliated deciduous teeth are completely different from any previously identified stem cells. Whereas SHED cells were isolated, from exfoliated deciduous teeth, the invention also includes multipotent cells obtained from deciduous teeth that have not exfoliated.

As described herein, SHED represent a novel population of postnatal stem cells capable of extensive proliferation and multi-potential differentiation. Deciduous teeth may, therefore, be an ideal resource of stem cells to repair damaged tooth structures, induce bone regeneration, and possibly to treat neural tissue injury or degenerative diseases, and to create fat when needed.

The invention also includes methods to generate dentin on pre-existing dentin. The method involves implanting dental stem cells onto pre-existing dentin. The dental stem cells can be dental pulp stem cells, or be human postnatal deciduous dental pulp multipotent stem cells. It has been discovered that implanted dental stem cells are able to form reparative dentin directly on the surface of pre-existing human dentin. Pulp-like tissue was also associated with the newly formed reparative dentin. In addition, odontoblasts and dentinogenic cells trapped inside the newly formed reparative dentin were immunopositive for a human dentin sialoprotein (DSP) antibody, and were shown by human-specific anti-mitochondrial staining to be derived from the implanted human DPSCs. The DPSCs also expressed angiogenic (blood vessel related) markers such as FGF receptor 1 and VEGF receptor 1. The expression of these markers indicates that DPSCs may also be involved in the creation of a pulp-like microenvironment to support the newly regenerated dentin. Accordingly, the first direct evidence to indicate that dental stem cells are able to generate reparative dentin on the surface of pre-existing human dentin is presented herein.

The newly discovered ability to generate reparative dentin on the surface of pre-existing dentin represents a great technical advance because it provides for the restorative generation of dentin within a tooth. This in turn has great practical value because it allows a dental or medical practitioner to provide better care to a patient in need of such treatment. For example, current protocols used during the performance of a dental root canal call for the removal of material, such as dentin and pulp, from the inside of a tooth to create a void, and then filling the void with an artificial material. A major defect in these types of protocols is that they produce an interface between the artificial material and the natural tissues found in the tooth. This interface can lead to infection and pain, and may require a patient to undergo further painful treatment and incur additional cost. Application of the invention to a root canal procedure allows human dental pulp stem cells to be placed into the void produced during the procedure. These cells will produce regenerative dentin on the surface of the pre-existing dentin, and will thereby avoid creating an interface of an artificial material with the pre-existing dentin. Thus, it is thought that use of the method of the invention can reduce costs and pain associated with dental treatment.

Definitions:

Abbreviations: Stein cells from human exfoliated deciduous teeth (SHED), Bone marrow stromal stem cell (BMSSC), Dental pulp stem cell from a permanent tooth (DPSC), phosphate buffered saline (PBS), bone morphogenic protein-4 (BMP-4), dentin sialoprotein (DSP), vascular endothelial growth factor (VEGF), basis fibroblast growth factor (bFGF), epidermal growth factor (EGF), alkaline phosphatase (ALP), matrix extracellular phosphoglycoprotein (MEPE), glutamic acid decarboxylase (GAD), glial fibrillary acidic protein (GFAP), neurofilament M (NFM), neuronal nuclei (NeuN), 2'-3'-cyclic nucleotide-3'-phosphodiesterase (CNPase).

An "acid solution" refers to a biocompatible liquid having a pH that is less than 7.0. The concentration of acid in an acid solution can have a broad range. Generally, the acid solution can be used to contact the surface of pre-existing dentin to remove materials that are inhibitory to the regenerative formation of dentin by dental stem cells. Accordingly, those of skill in the art can readily determine the concentration of acid that may be used in an acid solution. For example, the concentration can be between 0.01% and 100%, 1% and 10%, 1% and 5%, 0.5% and 2%, and values between the aforementioned ranges. Acid solutions within these ranges can be prepared based on volume (acid) to volume (diluent), mass (acid) to volume (diluent), or mass (acid) to mass (diluent), depending upon the methods used in the art to prepare a solution of a specific acid.

A "base solution" refers to a biocompatible liquid having a pH that is greater than 7.0. The concentration of base in a base solution can have a broad range. Generally, the acid solution can be used to contact the surface of pre-existing dentin to remove materials that are inhibitory to the regenerative formation of dentin by dental stem cells. Accordingly, those of skill in the art can readily determine the concentration of acid that may be used in an acid solution. For example, the concentration can be between 0.01% and 100%, 1% and 10%, 1% and 5%, 0.5% and 2%, and values between the aforementioned ranges. Base solutions within these ranges can be prepared based on volume (base) to volume (diluent), mass (base) to volume (diluent), or mass (base) to mass (diluent), depending upon the methods used in the art to prepare a solution of a specific base.

A "biological buffer" refers to a fluid which contains a buffering component which serves to maintain a constant pH. Numerous biological buffers are known in the art and have been described (Sambrook et al., *Molecular Cloning: A Laboratory Manual*, 3rd edition, Cold Spring Harbor Press, Cold Spring Harbor, N.Y. (2001)). Phosphate buffered saline is an example of a biological buffer.

A "biological solvent" is a biologically acceptable fluid that can be used to wash away a formulation used to prepare treated dentin, and which allows dental pulp stem cells to grow on the treated dentin. One example of a biologically acceptable solvent could be an ethanol solution. Those of skill in the art can readily determine biological solvents by washing pre-existing dentin with a candidate biological solvent, and determining if dental pulp stem cells are able to grow on the washed pre-existing dentin.

The term "carrier" refers to a vehicle with which a stem cell can be mixed prior to being implanted into an organism. Examples of carriers include, but are not limited to, gelatin, polyvinyl sponges, collagen matrices, and hydroxyapatite/tricalcium phosphate ceramics. Carriers can be prepared in numerous forms. For example, carriers can be formed into blocks, powders, strips, and the like. Carriers are known in the art and have been described (Krebsbach et al., *Transplantation*, 63:1059 (1997)).

A "dental stem cell" refers to a postnatal stem cell that is isolated from a human tooth. Dental stem cells can be isolated from a permanent tooth or a deciduous tooth.

The term "formulation" refers to a composition that can be used to prepare a surface of pre-existing dentin, or a region into which stem cells will be implanted, to allow implantation of dental pulp stem cells. Such a formulation can be used to remove materials from a surface or region that may interfere with implantation of a stem cell. Examples of interfering materials include cells, cell signaling molecules, peptides, and the like. In one embodiment, a formulation may be a 1% (w/v) acetic acid solution. A formulation can be readily determined by applying a test formulation to the surface of pre-existing dentin and determining whether dental pulp stem cells are able to attach and grow.

A "human postnatal deciduous dental pulp multipotent stem cell" refers to a stem cell that is isolated from a human deciduous tooth. Human postnatal deciduous dental pulp multipotent stem cells can be isolated from a deciduous tooth prior to exfoliation, or after exfoliation.

The term "isolated" means that a cell of the invention is not in the state found in nature. For example, the cell is sufficiently free of contaminants or other cell types with which a cell of the invention is naturally found. Moreover, an isolated cell of the invention may be present in a form that is sufficiently pure to be used therapeutically or for research. The term isolated does not require a cell of the invention to be free of all contaminants.

The term "mineralizing induction" refers to incubation of a stem cell in a culture medium which promotes action of the stem cell on other cell types, which causes the other cell types to form bone. Although not bound by any theory, the induced stem cells are thought to secrete factors that act on other cell types and promote bone formation by the other cell types. For example, a stem cell from a deciduous tooth (i.e. SHED) that has undergone mineralizing induction can stimulate a recipient cell to produce bone. An example of a medium that can be used for mineralizing induction includes L-ascorbate-2-phosphate, dexamethasone, and inorganic phosphate.

The term "neural induction" refers to incubation of a stem cell in a culture medium that promotes differentiation of the stem cell into a neural cell. An example of a medium that can be used for neural induction includes Neurobasal A, B27 supplement, 1% penicillin, epidermal growth factor, and fibroblast growth factor.

A "recipient cell" is a cell within an organism that becomes proximate to a stem cell when the stem cell is implanted into the organism. A recipient cell may be in direct contact with an implanted stem cell, or not in direct contact with the implanted cell but still influenced by the implanted cell. For example, an implanted human postnatal deciduous dental pulp multipotent stem cell may cause a recipient cell to form bone without actually contacting the recipient cell.

The term "trauma" refers to an event that causes a cell to undergo a detrimental change. Examples of trauma include, physical injury resulting from accident or medical treatment, disease, degeneration, and the like.

I. An Isolated Human Postnatal Deciduous Dental Pulp Multipotent Stem Cell

The invention provides isolated human postnatal deciduous dental pulp multipotent stem cells. These cells and methods to isolate them are disclosed herein. The cells can be isolated from deciduous teeth that are exfoliated, or non-exfoliated.

Human postnatal deciduous dental pulp multipotent stem cells can be grown in a tissue culture medium that includes serum. These cells can also be grown in serum free tissue culture media that contains bFGF. The serum free media may optionally contain EGF, and may optionally contain B27 supplement (GIBCO, Gaithersburg, Md.). Those of skill in the art can readily determine additional media in which the cells of the invention may be grown and maintained.

Human postnatal deciduous dental pulp multipotent stem cells can be collected and saved for future use through preservation techniques, such as freezing in liquid nitrogen. Methods for preserving cells are commonly used in the art. It is envisioned that such cells could be collected from the deciduous teeth of a human, saved, and implanted into the same human at a later time. Such a protocol would be useful for replacing cells lost due to age or trauma. For example, the saved cells could be used during dental reconstruction procedures later in life. In addition, cells can be treated with factors to induce them to form different phenotypes. In addition, the cells could be transfected with a nucleic acid construct that would cause the cells to express a desired product. These cells could then be implanted into the human in order to administer the desired product to the human. Examples of desired products include, but are not limited to, growth factors, hormones, cytokines, chemokines, factors related to hemophilia, and the like. Obtaining and implanting cells from the same individual is thought to avoid many complications resulting from immune rejection. Such method may also be applied to other dental stem cells, such as dental pulp stem cells.

Methods to prepare nucleic acid constructs are well known in the art and have been described (Sambrook et al., *Molecular Cloning: A Laboratory Manual*, 3rd edition, Cold Spring Harbor Press, Cold Spring Harbor, N.Y. (2001)).

Methods to transfect cells are well know in the art and include calcium phosphate co-precipitation, conventional mechanical procedures such as microinjection, electroporation, insertion of a plasmid encased in liposomes, or virus vectors, as well as others known in the art.

Accordingly, a dental stem cell, such as a human postnatal deciduous dental pulp multipotent stem cell or a dental pulp stem cell, can be transfected so that the cell expresses a desired product. The cell may then be implanted into an organism as described below such that the implanted cell expresses the desired product within the organism.

II. A Method to Produce Bone, Neural Tissue, Dentin, and Adipose Tissue within an Organism The invention provides a method to produce bone, neural tissue, dentin, and adipose tissue within an organism. The method for producing bone involves implanting a human postnatal deciduous dental pulp multipotent stem cell into the organism such that the postnatal stein cell is able to induce recipient cells to produce bone. The methods for producing neural tissue, adipose tissue, or dentin involve implanting a postnatal dental stem cell into the organism such that the desired product is formed. The postnatal dental stem cell may be a human postnatal deciduous dental pulp multipotent stem cell or a dental pulp stem cell as described herein.

The postnatal stem cells may be expanded ex vivo prior to being implanted into an organism. In addition, a postnatal stem cell of the invention may be implanted in combination, or not in combination with a carrier. Numerous carriers are known in the art and are available. An example of a carrier that may be used in accordance with the invention is hydroxyapatite/tricalcium phosphate. The dental stem cells of the invention can also be implanted in combination with a drug. For example, the cells may be implanted with an antibiotic, an antifungal, and the like. Numerous such drugs are known in the art (Merck Index, 13th edition, Whitehouse Station, N.J., 2001). Methods to preserve and implant cells are well known in the art.

The type of cell into which the postnatal stem cell differentiates is thought to depend upon the cellular environment into which the cell is implanted. For example, implantation of a postnatal stem cell of the invention into neural tissue is thought to cause the cell to differentiate into a neural cell. Alternatively, a postnatal stem cell of the invention can be cultured under inducing conditions to cause the postnatal stem cell to differentiate into a desired cell type. This culturing may be conducted prior to implantation of the differentiated, or partially differentiated cell, into an organism. For example, a postnatal stem cell of the invention may be subjected to mineralizing induction, induction with BMP-4, neuronal induction, or adipocyte induction.

The postnatal stem cells of the invention can be implanted into an organism to prevent or reduce numerous maladies. For example, a postnatal stem cell of the invention can be implanted into a void produced during a root canal procedure to promote the formation of dentin within a tooth. In another example, a postnatal stem cell of the invention may be implanted into neural tissue contained within an organism, such as a human, for the treatment of a neural degenerative disease or treatment of a neural injury. Neural degenerative disease are known in the art and are exemplified by Parkinson's disease and Alzheimer's disease. In another example, a postnatal stem cell of the invention may be implanted into the site of a physical neural injury to reduce the severity of the injury, or to promote healing of the injury. The protective and healing activity of the postnatal stem cells of the invention that differentiate into neural cells is thought to be due to the expression of neurotropic factors by the neural differentiated cells. In another example, a postnatal stem cell of the invention may be implanted into an organism to create fat when needed. Such fat creation can be used to reduce or ameliorate serious disorders (lyodystrophies) where fat is lacking in different or in all parts of the body. These patients often time experience severe problems related to energy metabolism, which is highly dependent upon fat.

The postnatal stem cells of the invention may be transfected with nucleic acid constructs that allow the transfected cells to express a desired product, as described above. Accordingly, these transfected cells may be implanted into an organism prior to, or after being differentiated, such that the cells match the cell type of the cells at the implantation site.

III. A Method to Generate Dentin on a Pre-Existing Dentin

The invention provides a method to generate dentin on pre-existing dentin. Generally, the method involves contacting pre-existing dentin with dental stem cells and incubating the pre-existing dentin with the dental stem cells under conditions where the dental stem cells grow and produce dentin. The postnatal dental stem cell may be a human postnatal deciduous dental pulp multipotent stem cell or a dental pulp stem cell as described herein.

Such incubation conditions are disclosed herein (Example 1). In addition, those of skill in the art can readily contact pre-existing dentin with dental stem cells under various test conditions to determine incubation conditions in which dental stem cells produce dentin.

Methods to isolate dental stem cells have been disclosed (Example 1) (Gronthos et al., *Proc. Natl. Acad. Sci. USA*, 97: 13625-13630 (2000); Gronthos et al., *J. Dent. Res.*, 81:531-535 (2002)). The dental stem cells may be obtained from an organism, such as a human, that is different than the organism into which the cells will be implanted. Alternatively, dental stem cells may be obtained from the same organism, such as a human, into which they will be implanted. Immune rejection of implanted cells may be avoided by obtaining cells from the same organism into which the cells will be implanted.

The method may be practiced in vitro under tissue culture conditions. Briefly, dentin may be placed in tissue culture media, contacted with dental stem cells, and incubated under conditions where the dental stem cells will produce dentin. Tissue culture media that is able to support dental stem cells has been disclosed in the Example section herein, and in the art (Gronthos et al., *Proc, Natl. Acad, Sci. USA*. 97: 13625-13630 (2000); Gronthos et al., *J. Dent. Res.*, 81:531-535 (2002)). Such in vitro methods may be useful for preparing an implant that contains dentin in association with live dental stem cells. Such an implant may be inserted into a void that is produced during a root canal procedure in order to promote the formation of regenerative dentin.

The method may be practiced under in vivo conditions. Briefly, dental stem cells may be grown under tissue culture conditions and then collected. The collected cells may then be contacted with pre-existing dentin contained within an organism such that the dental stem cells produce dentin. For example, the collected cells may be inserted into a void that is produced during a root canal procedure. The tooth containing the void into which the cells were inserted can then be sealed through use of many art recognized methods, such as use of an epoxy resin, and as disclosed herein (Example 2).

The dental stem cells may be contacted with pre-existing dentin in combination with a carrier, or not in combination with a carrier. Numerous carriers are known in the art and are disclosed herein. An example of a carrier that may be used is hydroxyapatite/tricalcium phosphate.

Pre-existing dentin may be contacted with a formulation prior to being contacted with the dental stem cells. Such a formulation may remove cells and other materials that may interfere with the interaction of the dental stem cells with the pre-existing dentin, or that act to inhibit the growth of the dental stem cells. An example of a formulation that may be used is a 1% (v/v) aqueous solution of acetic acid. Other formulations may be used to prepare pre-existing dentin prior to contacting the dentin with dental stem cells. Examples of such formulations include acid solutions and basic solutions. Those of skill in the art can readily determine formulations that promote the growth of dental stem cells on pre-existing dentin by contacting dentin with a test formulation, incubating dental stem cells with dentin, and determining if the dental stem cells produce dentin.

Pre-existing dentin may be contacted with a formulation, and then washed with a fluid. The fluid may wash away the formulation as well as cellular debris and other materials that may interfere with the interaction of the dental stem cells with the pre-existing dentin, or that act to inhibit the growth of the dental stem cells. Numerous fluids may be used to wash the pre-existing dentin. Examples of such fluids include, but are not limited to, water, biological solvents, and biological buffers. An example of a specific biological buffer is phosphate buffered saline.

Regenerative dentin production allows biological material to be replaced with newly formed biological material as opposed to artificial materials. This may avoid an immune or allergic reaction to an artificial material that is implanted into an organism. In addition, biological materials may be better maintained over time than artificial materials due to continuous cellular turnover.

Example 1

Obtaining Dental Pulp Stem Cells (DPSC) and Cell Culture Thereof

Human impacted third molars were collected from adults (19-29 years of age) at the Dental Clinic of the National Institute of Dental & Craniofacial Research under approved guidelines set by the NIH Office of Human Subjects Research. Human DPSCs were isolated and cultured as previously described (Gronthos et al., *Proc. Natl. Acad. Sci. USA*, 97: 13625-13630 (2000); Gronthos et al., *J. Dent. Res.*, 81:531-535 (2002)). Briefly, the pulp tissue was separated from the crown and root and then digested in a solution of 3 mg/ml collagenase type I (Worthington Biochem, Freehold, N.J.) and 4 mg/ml dispase (Boehringer Mannheim, GMBH, Germany) for one hour at 37° C. $2 \times 10^4$ cells were seeded into 6-well plates (Costar, Cambridge, Mass.) with alpha Modification of Eagle's Medium (GIBCO BRL, Grand Island, N.Y.) supplemented with 15% fetal calf serum (Equitech-Bio Inc, Kerrville, Tex.), 100 µM L-ascorbic acid 2-phosphate (WAKO, Tokyo, Japan), 2 mM L-glutamine, 100 U/ml penicillin and 100 µg/ml streptomycin (Biofluids Inc, Rockville, Md.), then incubated at 37° C. in 5% $CO_2$.

Example 2

Implantation of Dental Pulp Stem Cells

The root of the third molars were cut to expose the pulp chamber, a thin layer of pulpal dentin surface was removed using a carbide bur, the exposed surface was treated with 1% acetic acid for 10 minutes at room temperature, and then washed three times with PBS. The thin layer of pulpal dentin was removed in order to remove any possible remaining pulp tissue, especially odontoblasts. Approximately $2.0 \times 10^6$ DPSCs at 25-35 population doublings were loaded on to the acid-treated/PBS washed dentin surface and incubated under the cell culture medium at 37° C. for 12 hours (FIG. 1). The root foramen was sealed with Gelfoam (absorbable gelatin sponge, Pharmacia & Upjohn Company, Kalamazoo, Mich.) and the culture medium was removed before the implantation. The dentin/DPSC complexes were then implanted subcutaneously under the dorsal skin of 10-week-old immunocompromised beige mice (NIH-bg-nu-xid, Harlan Sprague Dawley, Indianapolis, Ind.) (FIG. 1). Non-acid treated dentin-DPSC implants and acid-treated/PBS washed dentin cultured with skin fibroblasts ($2.0 \times 10^6$) were used as controls. These procedures were performed in accordance to specifications of an approved small animal protocol (NIDCR #00-113). The implants were recovered at 8 weeks post-implantation, fixed with 4% formalin, decalcified with buffered 10% EDTA (pH 8.0), and then embedded in paraffin. Sections (5 µm) were deparaffinized and stained with hematoxylin and eosin.

Acid-treated human dentin scaffold, as a negative control, did not induce any significant host cellular components in vivo (FIG. 1A). Also, skin fibroblasts failed to generate any mineralized tissue on the surface of the human dentin scaffold (FIG. 2B). In contrast, DPSCs were capable of generating reparative dentin directly on the surface of human dentin when they were co-implanted into immunocompromised mice after acid treatment and 12 hours pre-incubation (FIG. 2C-E). Reparative dentin formation was initiated on the acid-treated human dentin surface that provided a scaffold for the dentinogenesis of DPSCs. Newly formed reparative dentin could be generated by odontoblasts only (FIG. 2E) or formed by odontoblasts with dentinogenic cells trapped inside the reparative dentin (FIG. 2C-D). Newly formed reparative dentin was associated with a cell rich pulp-like tissue containing blood vessels and, in some areas, a significant amount of red blood cells (FIG. 2C-D), which is distinctive to the connective tissue that has no association with reparative dentin formation (FIG. 2A-D). Like most regenerative dentin, the newly formed dentin did not form an organized dentinal tubule structure, a result different from that shown in DPSC/HA/TCP implants (FIG. 2F). Nine DPSC/dentin complexes were implanted into immunocompromised mice, 3 out of 8 (37.5%) implanted DSPC/dentin complexes clearly showed reparative dentin formation on the sections examined. The rate of reparative dentin formation is estimated to be higher than 37.5% if all implants were completely examined through a series histology section.

Example 3

Immunohistochemistry Dental Pulp Stem Cells

Primary DPSCs were sub-cultured into 8-chamber slides ($2 \times 10^4$ cells/well) (NUNC Inc, Naperville, Ill.). After 5 days culture at 25 population doublings, the cells were fixed in freshly prepared 4% formalin for 15 minutes then washed in PBS. The samples were subsequently blocked with 5% non-immune goat serum for 1 hour at room temperature. Samples were incubated with primary antibodies in 5% non-immune goat serum for 1 hour at room temperature. Antibodies used were against: Flg (1:200 dilution; rabbit anti-FGF receptor 1, Santa Cruz Biotechnology, Santa Cruz, Calif.), and Flt1 (1:200 dilution; rabbit anti-VEGF receptor 1, Santa Cruz Biotechnology, Santa Cruz, Calif.). After washing, the samples were incubated with goat anti-rabbit IgG-Rhodamine Red (Jackson ImmunoResearch, West Grove, Pa.), for 45 minutes at room temperature, washed and mounted in VECTASHIELD fluorescence mountant.

The DPSC implant sections were treated with hydrogen peroxide to eliminate endogenous peroxidase. Sections were incubated with the primary antibodies at room temperature for 1 hour. Primary antibodies used were against: mitochondria (1:100 dilution; rabbit anti-human-specific, Chemicon, Temecula, Calif.); dentin sialoprotein (1:400 dilution; LF-151, rabbit anti-human DSP) (Gronthos et al., *J. Dent. Res.*, 81:531-535 (2002)). Histostain SP Kits were used for biotinylated second antibodies and enzyme conjugate incubation according to the instructions (Zymed Laboratories Inc. South San Francisco, Calif.).

In order to characterize the newly regenerated reparative dentin on the pre-existing human dentin surface, immunohistochemical staining was used to show that dentin scaffold and the dentinogenic cells of the newly formed reparative dentin were positive for DSP antibody staining (FIGS. 3A and 3B). Pulp-like tissue and connective tissue failed to show immunopositive staining for DSP antibody (FIGS. 3A and 3B). Only the peritubular dentin structure of the dentin scaffold was immunoreactive to DSP antibody. Therefore, the matrix of newly formed reparative dentin without tubular dentin structure failed to show a positive immunostaining for DSP antibody (FIG. 3B). Human-specific anti-mitochondria immunohistochemistry was used to identify human cells and their pattern of distribution in the DPSC/dentin implants. After 8 weeks, the human DPSCs were capable of differentiating into odontoblasts and becoming dentinogenic cells trapped inside the newly formed reparative dentin (FIGS. 3C and 3D).

Figures 4A, 4B:

It is thought that DPSCs interact with host cells to initiate the formation of the dentin and pulp-like tissue. In regenerating a dentin/pulp-like complex, the donor cells are thought to stimulate host cells to create a microenvironment, a part of which is the vasculature. Therefore whether DPSCs expressed some angiogenesis associated cell receptors was examined. It was determined that DPSCs expressed FGF receptor 1 and VEGF receptor 1 by immunohistochemical staining (FIG. 4A-B). Most of cultured DPSCs expressed FGF receptor 1 (FIG. 4A) and, in contrast, the number of VEGF receptor 1 positive DPSCs were limited (FIG. 4B). Furthermore, dentinogenic cells in the DPSC/dentin implants showed immunopositive staining for FGF receptor 1 and VEGF receptor 1 (FIGS. 4D and 4E).

Example 4

Western Blot of Dental Pulp Stem Cells

Lysates prepared from culture DPSCs at 25-35 population doublings were separated on a 12% Tris-Glycine SDS-PAGE gel (Novex, San Diego, Calif.). The proteins were then transferred onto BA-S 85 nitrocellulose membranes (Schleicher & Schuell, Keene, N.H.) and blocked for 1 hour at room temperature in 3% (w/v) BSA and 3% normal goat serum. Primary antibodies of Flg (1:500 dilution) and Flt (1:500 dilution) were the same as those used for immunohistochemical staining. HSP90 (1:100 dilution, rabbit anti-HSP90, Santa Cruz Biotechnology, Santa Cruz, Calif.) was used as control to confirm protein loading. Filters were washed then incubated with a 1:50,000 dilution of goat-anti rabbit IgG conjugated to HRP (Kirkegaard & Perry Laboratories Inc., Gaithesburg, Md.) for 1 hour at room temperature. Following immunolabeling, the membranes were washed and reacted with Super Signal chemiluminescence HRP substrate (Pierce Chemical Co., Rockford, Ill.) according to the manufacturer's recommendations and then analyzed using Kodak X-Omat film, (Kodak, Rochester, N.Y.).

Western blot analysis indicated that DPSCs expressed FGF receptor and VEGF receptor (FIG. 4C).

Example 5

Antibodies Used to Characterize Human Postnatal Deciduous Dental Pulp Multipotent Stem Cells (Inclusive of SHED)

Rabbit antibodies included anti-HSP90, bFGF (Santa Cruz Biotechnology, Inc., Santa Cruz, Calif.); anti-CBFA1 (Oncogene Research Product, Cambridge, Mass.); anti-endostatin, human-specific mitochondria, GAD (Chemicon, Temecula, Calif.); anti-alkaline phosphatase (LF-47), bone sialoprotein (LF-120), MEPE (LF-155), dentin sialophosphoprotein (LF-151) from NIDCR/NIH. Goat antibodies included anti-MAP2 and Tau (Santa Cruz Biotechnology). Mouse antibodies included anti-STRO-1, CD146 (CC9); GFAP (glial fibrillary acidic protein), Nestin, Neurofilament M (NFM), NeuN, CNPase (Chemicon, Temecula, Calif.); and anti-$\beta$III tubulin (Promega, Madison, Wis.). Rabbit and murine isotype-matched negative control antibodies were also used (Caltag Laboratories, Burlingame, Calif.).

Example 6

Collection and Cell Culture of Human Postnatal Deciduous Dental Pulp Multipotent Stem Cells Normal exfoliated human deciduous incisors were collected from 7-8 year old children under approved guidelines set by the National Institutes of Health Office of Human Subjects Research. The pulp was separated from a remnant crown and then digested in a solution of 3 mg/ml collagenase type I (Worthington Biochem, Freehold, N.J.) and 4 mg/ml dispase (Boehringer Mannheim, GMBH, Germany) for one hour at 37° C. Single cell suspensions were cultured in a regular medium as previously reported (Gronthos et al., *Proc. Natl. Acad. Sci. USA*, 97: 13625-13630 (2000)). These techniques resulted in a population that we have termed SHED (stem cells from human exfoliated deciduous teeth).

Here it is demonstrated that the remaining crown of exfoliated deciduous teeth contains a living pulp remnant comprised of a normal dental pulp including connective tissue, blood vessels, and odontoblasts (FIG. 5A-C). In order to isolate stem cells, single cell suspensions were derived from the remnant pulp and placed at low density in liquid culture. About 12 to 20 cells from each exfoliated incisor were capable of forming adherent colonies (FIG. 5D), characteristic of other stromal stem cell populations (Gronthos et al., *Proc. Natl. Acad. Sci. USA*, 97: 13625-13630 (2000)).

When compared to adult bone marrow stromal stem cells (BMSSCs) and dental pulp stem cells (DPSCs), SHED showed a higher proliferation rate (FIG. 5G) and a higher number of population doublings (FIG. 5H).

Figures 6A, 6B, 6C, 6D, 6E, 6F, 6G, 6H, 6I, 6J, 6K, 6L, 6M:
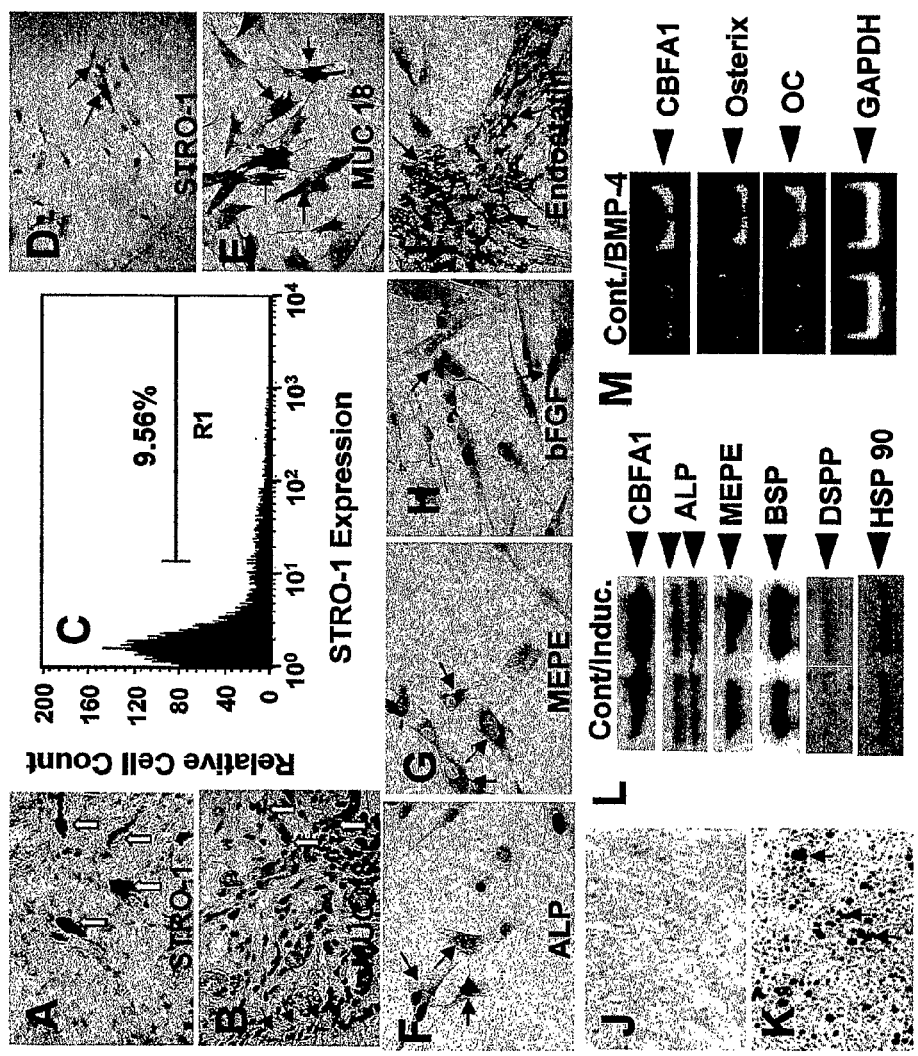
FIGS. 6A-6M show that SHED possess stem cell characteristics. (A-E) The remnant pulp showed STR0-1 (open arrows in A) and CD146 (open arrows in B) immunopositive staining for cells in perivascular areas. FACS analysis showed that ex vivo expanded SHED contained approximately 9% STR0-1 positive cells (C). SHED expressed STR0-1 (D) and CD146 (E) (arrows). (F-I) SHED expressed osteogenic and angiogenic markers ALP, MEPE, bFGF, and endostatin. (J and K) SHED were either cultured with regular medium (J) or cultured with L-ascorbate-2-phosphate, dexamethasone, and inorganic phosphate for 4 weeks (K). Alizarin red staining showed mineralized nodule formation in the induction (K). (L) Western blot analysis showed an up-regulated expression of CBFA1, ALP, MEPE, BSP, and DSPP following the induction as described herein. HSP90 was used to assess the amount of protein loaded per sample. (M) Human recombinant BMP-4 (300 ng/ml, 24 hours) was added to induce a significant up-regulation of CBFA1, Osterix, and osteocalcin (OC) in SHED as detected by semi-quantitative PCR.

Ex vivo expanded SHED were found to express the cell surface molecules STRO-1 and CD146 (MUC18), two early mesenchymal stem cell markers previously found to be present in BMSSCs and DPSCs (FIGS. 6D and 6E). STRO-1 and CD146 positive cells were found to be located around blood vessels of the remnant pulp by immunohistochemical staining (FIGS. 6A and 6B), implying that SHED may have originated from a perivascular microenvironment. A minor proportion (9%) of ex vivo expanded SHED stained positive for the STRO-1 antibody using FACS analysis (FIG. 6C). Further immunohistotypic analysis demonstrated that cultured SHED expressed stromal and vascular related markers ALP, MEPE, bFGF, and endostatin (FIG. 6F-6I).

Conditions for the induction of calcium accumulation were as reported previously (Gronthos et al., *Proc. Natl. Acad. Sci. USA,* 97: 13625-13630 (2000)), and recombinant human BMP-4 (R&D systems, Minneapolis, Minn.) was used to induce osteogenic differentiation. Calcium accumulation was detected by 2% Alizarin Red S (pH 4.2) staining. The calcium concentration was measured using a commercially available kit (Sigma Calcium Kit #587-A).

To investigate the potential of SHED to differentiate into mineralized tissue, established secondary SHED cultures were supplemented with L-ascorbate-2-phosphate, dexamethasone, and inorganic phosphate as previously described (Gronthos et al., *Proc. Natl. Acad. Sci. USA,* 97: 13625-13630 (2000)). Alizarin Red-positive nodules formed in the SHED cultures following four weeks of induction (FIGS. 6J and 6K), indicating calcium accumulation in vitro. Accordingly, Western blot analysis revealed that various bone markers CBFA1, ALP, MEPE and BSP were up-regulated under the induction (FIG. 6L). In addition, DSPP was induced by the mineralizing induction (FIG. 6L). Furthermore, BMP-4 treatment was capable of inducing an up-regulated expression of CBFA1, Osterix, and Osteocalcin (OC) by semi-quantitative RT-PCR (FIG. 6M). These data indicated that SHED possessed the ability to differentiate into functional odontoblast-like cells in vitro.

Figures 10A, 10B:
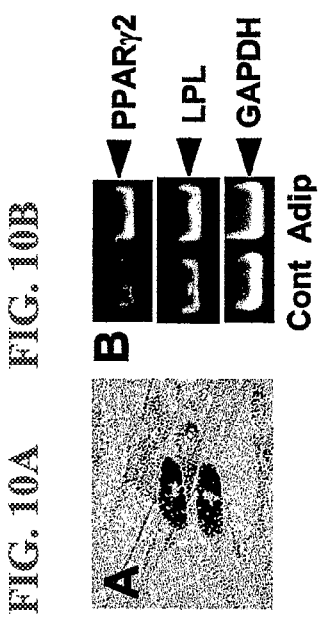
FIGS. 10A-10B illustrate the adipogenic differentiation of SHED. Cultured SHED formed Oil red 0 positive lipid clusters following five weeks of induction in the presence of 0.5 mM isobutylmethylxanthine, 0.5 μM hydrocortisone, and 60 μM indomethacin (A). A significant up-regulation of PPARγ2 and lipoprotein lipase (LPL) was observed in the group induced with the adipogenic cocktail (Adip) as compared to the control group (Cont) by RT-PCR (B).

SHED cells were induced for adipogenesis with procedures used with different cells (Gimble et al., *J. Cell. Biochem.,* 58:393-402 (1995)). Following five weeks of culture with an adipogenic inductive cocktail, around 5% of cultured SHED were found to possess the potential to develop into Oil red O-positive lipid-laden fat cells (FIG. 10A). This correlated with an up-regulation in the expression of two adipocyte specific transcripts, PPARγ2 and lipoprotein lipase (LPL), as detected by semi-quantitative RT-PCR (FIG. 10B).

For neural differentiation, Neurobasal A (Gibco-BRL), B27 supplement (Gibco-BRL), 1% penicillin, EGF 20 ng/ml (BD Bioscience), FGF 40 ng/ml (BD Bioscience) were used to culture cells attached to 0.1% gelatin-coated dishes (StemCell Technologies Inc, Vancouver, Canada). For sphere-like cell cluster formation, 3% rat serum and B27 were added.

When cultured either under a neuronal differentiation condition or in 3% rat serum with B27 supplement, these cells formed sphere-like clusters (FIG. 5E) in which highly proliferative cells aggregated together in clusters which either adhered to the culture dish or floated freely in the culture medium. After separating the sphere-like clusters, the cells were able to grow as individual fibroblastic cells (FIG. 5F).

The potential of SHED to develop into neural cells was determined. To elucidate the neural differentiation potential of SHED, the expression of neural markers in SHED was examined. It was determined that cultured SHED expressed a variety of neural cell markers including Nestin, beta III tubulin, GAD, NeuN, GFAP, NFM, and CNPase as measured by immunocytochemical staining (FIG. 8A-8H) and Western blot analysis (FIG. 8I). After four weeks of neural inductive culture, expression levels of neuronal markers including beta III tubulin, GAD, and NeuN were increased, while the levels of Nestin, GFAP, NFM, and CNPase remained unchanged (FIG. 8I). When cultured under these conditions, SHED lost their fibroblastic morphology and developed multi-cytoplasmic processes correlating with either beta III tubulin/GAD or beta III tubulin/NFM expression (FIG. 8J-8O). The long cellular processes could be best viewed following toluidine blue staining and were immunoreactive to MAP2 and Tau antibodies (FIG. 8P-8S). Following the neural inductive culture, SHED continued to express glial cell makers such as Nestin, CNPase, GFAP, and NFM (FIG. 8T-8W).

Example 7

Implantation of Human Postnatal Deciduous Dental Pulp Multipotent Stem Cells

Approximately $2.0 \times 10^6$ SHED were mixed with 40 mg of hydroxyapatite/tricalcium phosphate (HA/TCP) ceramic powder (Zimmer Inc, Warsaw, Ind.) and then implanted subcutaneously into immunocompromised mice (NIH-bg-nu-xid, Harlan Sprague Dawley, Indianapolis, Ind.) as previously described (Krebsbach et al., *Transplantation,* 63: 1059-1069 (1997)).

To validate the capacity of SHED to form odontoblasts, ex vivo expanded SHED were implanted into immunocompromised mice (Gronthos et al., *Proc. Natl. Acad. Sci. USA,* 97: 13625-13630 (2000); Gronthos et al., *J. Dent. Res.,* 81:531-535(2002)). The implants yielded human-specific alu-positive odontoblasts directly associated with a dentin-like structure (FIGS. 7A and 7B). The regenerated dentin was immunoreactive to dentin-specific DSPP antibody (FIG. 7C). These findings indicated that human SHED satisfies one important stem cell attribute; the ability to differentiate into odontoblasts in vivo. However, SHED were unable to regenerate a complete dentin-pulp-like complex as do DPSCs in vivo (FIGS. 7A and 7E). In addition, SHED were capable of inducing recipient murine cells to differentiate into bone-forming cells as noted by murine-specific pf1 in situ hybridization (FIG. 7L), and lacked DSPP expression (FIG. 7D). Skin fibroblasts were never capable of inducing bone formation upon in vivo implantation. Accordingly, it is thought that SHED are distinctively different from DPSC in respect to the odontogenic differentiation and osteogenic induction.

The characteristics of clonal cell strains, each originating from a single cell of deciduous pulp were then determined. When twelve single-colony derived SHED clones were implanted into immunocompromised mice, only one fourth (3/12) of the clones demonstrated a potential to generate ectopic dentin-like tissue on the HA/TCP carrier equivalent to that generated by multi-colony derived SHED (FIGS. 7E and 7G). SHED either from single-colony or from multi-colony were found to form dentin-like tissue (FIG. 7F) and to survive in the fibrous tissue within the implants (FIG. 7H) as demonstrated by human-specific alu in situ hybridization. These results infer that SHED may contain subpopulations of cells, either differentiating into odontoblasts or residing in the connective tissue compartments. Surprisingly, all implanted single-colony derived SHED clones were capable of inducing bone formation in immunocompromised mice. About 40% of the clonal cell strains (5/12) induced a significant amount of new bone, while the remaining 60% (7/12) induced a limited amount of bone (FIGS. 7I and 7J). SHED were found to be located on the surfaces of HA/TCP but did not participate in bone formation as indicated by human-specific alu in situ hybridization (FIG. 7K). In contrast, murine host cells were found to differentiate into osteoblasts and osteocytes as shown by reactivity to murine-specific pf1 in situ hybridization (FIG. 7L).

SHED were injected into the brain of immunocompromised mice according to specifications of an approved small animal protocol (NIDCR#01-185). Coordinates for the target sites were determined by referencing a murine brain atlas (Paxinos G et al, $2^{nd}$ E, 2001) (see FIG. 9A). The anteroposterior (AP), mediolateral (ML), and dorsoventral (DV) coordinates were computed relative to Bregma. Ex vivo expanded SHED (10,000 cells/μl) were infused to the dentate gyrus of the hippocampus (Benedetti et al., Nat. Med., 6:447-450 (2000); Seri et al., Neurosci., 21:7153-7160 (2001)). Cells (0.5 μl/side) were infused to the coordinates (AP, ML, DV, respectively: −1.5 mm, +/−0.8 mm, and 2.0 mm) using a 1 μl Hamilton Syringe.

Figures 9A, 9B:
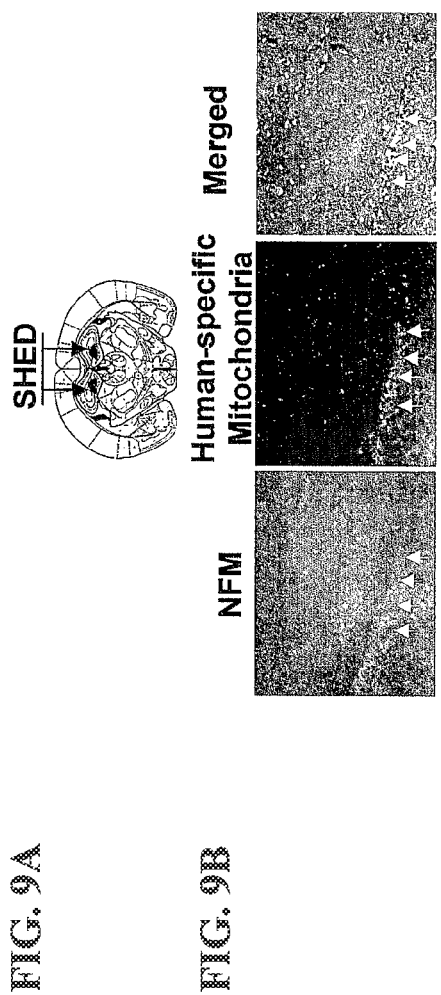
FIGS. 9A-9B show implantation of SHED into the brain. (A) Diagram indicating injection of SHED into the dentate gyrus of the hippocampus. (B) SHED were cultured in the neural differentiation medium as described in the Methods for one week, after which 5,000 cells in 0.5 μl PBS were injected into the dentate gyrus of the hippocampus of immunocompromised mice. After 10 days, the brain was fixed and prepared for immunofluorescence staining with NFM and human-specific anti-mitochondrial antibody. The anti-mitochondrial antibody immunostaining showed human SHED (arrows, middle panel, green in color photo) in the dentate gyrus of the hippocampus with co-expression of neurofilament (arrows, left panel, red in color photo). In merged images, co-expression of human mitochondria and NFM showed co-localization of antigen expression as indicated by arrows (yellow in color photo). Magnification 20×.

Neural developmental potential was further studied in vivo by injecting SHED into the dentate gyrus of the hippocampus of immunocompromised mice (FIG. 9A). Histological examination showed that SHED survived for over 10 days inside the mouse brain microenvironment as noted by human-specific anti-mitochondria antibody staining and continued to express neural markers such as NFM (FIG. 9B).

Example 8

Reverse Transcriptase-Polmerase Chain Reaction Used to Characterize Human Postnatal Deciduous Dental Pulp Multipotent Stem Cells The PCR primers included: PPARγ2 sense, 5'-CTCCT-ATTGACCCAGAAAGC-3' (SEQ ID NO: 1)(114-133), antisense, 5'-GTAGAGCTGAGTCTTCTCAG-3' (SEQ ID NO: 2)(441-460, Genbank accession number: XM_003059); LPL sense, 5'-ATGGAGAGCAAAGCCCTGCTC-3' (SEQ ID NO: 3)(175-195), antisense, 5'-GTTAGGTCCAGCTG-GATCGAG-3' (SEQ ID NO: 4)(718-738, Genbank accession number: XM_044682); Core-binding factor, runt domain, alpha subunit 1 (CBFA1) sense, 5'-CAGTTC-CCAAGCATTTCATCC-3' (SEQ ID NO: 5)(880-900), antisense, 5'-TCAATATGGTCGCCAAACAG-3' (SEQ ID NO: 6)(1304-1323, Genbank accession number: L40992); Osterix sense, 5'-GCAGCTAGAAGGGAGTGGTG-3' (SEQ ID NO: 7)(821-840), antisense, 5'-GCAGGCAGGT-GAACTTCTTC-3' (SEQ ID NO: 8)(1160-1179, Genbank accession number: XM_062600); Osteocalcin sense, 5'-CATGAGAGCCCTCACA-3' (SEQ ID NO: 9)(18-33), antisense, 5'-AGAGCGACACCCTAGAC-3' (SEQ ID NO: 10) (316-332, Genbank accession number: X53698); GAPDH sense, 5'-AGCCGCATCTTCTTTTGCGTC-3' (SEQ ID NO: 11)(12-32), antisense, 5'-TCATATTTGGCA-GGTTTTTCT-3' (SEQ ID NO: 12)(807-827, Genbank accession number: M33197). Total RNA isolation, first-strand cDNA synthesis and PCR processes were as previously described (Gronthos et al., J. Dent. Res., 81:531-535 (2002)).

Example 9

In Situ Hybridization Used to Characterize Human Postnatal Deciduous Dental Pulp Multipotent Stem Cells Human-specific alu and murine-specific pf1 sequences labeled with digoxigenin were used as probes for in situ hybridization as previously described (Gronthos et al., Proc. Natl. Acad. Sci. USA, 97: 13625-13630 (2000)). Primers included: human alu, sense, 5'-TGGCTCACGCCTG-TAATCC-3' (SEQ ID NO: 13)(90-108), antisense, 5'-TTTTTTGAGACGGAGTCTCGC-3' (SEQ ID NO: 14) (344-364, Genbank accession number: AC004024); and murine pf1, sense, 5'-CCGGGCAGTGGTGGCGCATGC-CTTTAAATCCC-3' (SEQ ID NO: 15)(170-201), antisense, 5'-GTTTGGTTTTTGAGCAGGGTTCTCTGTGTAGC-3' (SEQ ID NO: 16)(275-306, Genbank accession number: X78319).

We claim:

1. A method to produce human neural cells that express neural markers in a subject, comprising
    implanting into brain tissue of the subject an isolated population of human postnatal deciduous dental pulp multipotent stem cells, wherein
    the human postnatal deciduous dental pulp multipotent stem cells are from a postnatal deciduous tooth;
    human postnatal deciduous dental pulp multipotent stem cells in the population differentiate into a neural cell;
    human postnatal deciduous dental pulp multipotent stem cells in the population can proliferate to over 140 population doublings; and
    the isolated population of human postnatal deciduous dental pulp mulitpotent stem cells were expanded ex vivo, wherein the human postnatal deciduous dental pulp multipotent stem cells in the population express CD146,
    thereby allowing the human postnatal deciduous dental pulp cells to give rise to human neural cells that express neural markers in the brain tissue of the subject.

2. The method of claim 1, wherein human postnatal deciduous dental pulp multipotent stem cells within the population express STRO-1.

3. The method of claim 1, wherein the human postnatal deciduous dental pulp multipotent stem cells are transfected with an exogenous nucleic acid segment that encodes a heterologous product, and wherein the cells express the product.

4. The method of claim 1, wherein the postnatal deciduous tooth is an incisor.

5. The method of claim 1, wherein the isolated population of human postnatal dental pulp cells were obtained by the process of:
    separating pulp from a remnant crown of a human postnatal deciduous tooth;
    digesting the pulp in collagenase and dispase to form digested pulp;
    producing a single cell suspension from the digested pulp;
    isolating single cells that adhere to a tissue culture surface from the single cell suspension; and
    culturing the single cells in vitro.

6. The method of claim 1, wherein human postnatal deciduous dental pulp multipotent stem cells within the population do not express STRO-1.

7. The method of claim 1, wherein the subject has neural trauma.

8. The method of claim 1, wherein the subject has a neural degenerative disease or a physical injury.

9. The method of claim 8, wherein the neural degenerative disease is Alzheimer's disease or Parkinson's disease.

10. A method for producing neural cells in a subject, comprising implanting, into a brain of the subject, a composition comprising a biocompatible three dimensional carrier and a mixed population of human postnatal deciduous dental pulp multipotent stem cells that have been cultured ex vivo, induce formation of bone growth when implanted in vivo, and can proliferate for over 140 population doublings, wherein the human postnatal deciduous dental pulp multipotent stem cells in the population express CD146,
    thereby allowing the human postnatal deciduous dental pulp cells to give rise to neural cells in the brain of the subject.

11. The method of claim 10, further comprising
    transfecting the human postnatal deciduous dental pulp multipotent stem cells with an exogenous nucleic acid segment that encodes a heterologous product, wherein the human postnatal deciduous dental pulp multipotent stem cells express the product, prior to implanting the human postnatal deciduous dental pulp multipotent stem cells into the subject.

12. The method of claim 10, wherein the subject has neural trauma.

13. The method of claim 10, wherein the subject has a neural degenerative disease or a physical injury.

14. The method of claim 13, wherein the neural degenerative disease is Alzheimer's disease or Parkinson's disease.

15. The method of claim 10, wherein the biocompatible carrier is gelatin, a polyvinyl sponge, a collagen matrix, or a hydroxyapatite/tricalcuim phosphate ceramic.

16. The method of claim 10, wherein the composition is a sterile implantable solution.

17. The method of claim 10, wherein human postnatal deciduous dental pulp multipotent stem cells within the population express STRO-1.

18. The method of claim 10, wherein human postnatal deciduous dental pulp multipotent stem cells within the population do not express STRO-1.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ctcctattga cccagaaagc                                               20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gtagagctga gtcttctcag                                               20

<210> SEQ ID NO 3
<211> LENGTH: 21
<212> TYPE: DNA
<213> ORGANISM: Artificial Sequence
<220> FEATURE:
<223> OTHER INFORMATION: Primer
```

```
<400> SEQUENCE: 3
atggagagca aagccctgct c                                              21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gttaggtcca gctggatcga g                                              21

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
cagttcccaa gcatttcatc c                                              21

<210> SEQ ID NO 6
<211> LENGTH: 20
<212> TYPE: DNA
<213> ORGANISM: Homo sapiens

<400> SEQUENCE: 6
tcaatatggt cgccaaacag                                                20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gcagctagaa gggagtggtg                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gcaggcaggt gaacttcttc                                                20

<210> SEQ ID NO 9
<211> LENGTH: 16
<212> TYPE: DNA
<213> ORGANISM: Artificial Sequence
<220> FEATURE:
<223> OTHER INFORMATION: Primer

<400> SEQUENCE: 9
catgagagcc ctcaca                                                    16

<210> SEQ ID NO 10
<211> LENGTH: 17
<212> TYPE: DNA
```

```
<213> ORGANISM: Artificial Sequence
<220> FEATURE:
<223> OTHER INFORMATION: Primer

<400> SEQUENCE: 10
agagcgacac cctagac                                                  17

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
agccgcatct tcttttgcgt c                                             21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tcatatttgg caggtttttc t                                             21

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
tggctcacgc ctgtaatcc                                                19

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14 tttttgaga cggagtctcg c                                              21

<210> SEQ ID NO 15
<211> LENGTH: 32
<212> TYPE: DNA
<213> ORGANISM: Artificial Sequence
<220> FEATURE:
<223> OTHER INFORMATION: Primer

<400> SEQUENCE: 15
ccgggcagtg gtggcgcatg cctttaaatc cc                                 32

<210> SEQ ID NO 16
<211> LENGTH: 32
<212> TYPE: DNA
```

```
<213> ORGANISM: Artificial Sequence
<220> FEATURE:
<223> OTHER INFORMATION: Primer

<400> SEQUENCE: 16
gtttggtttt tgagcagggt tctctgtgta gc                                      32
```